(12) United States Patent
Clark et al.

(10) Patent No.: US 7,488,604 B2
(45) Date of Patent: Feb. 10, 2009

(54) APPARATUS AND METHODS FOR LIQUID SAMPLE HANDLING BASED ON CAPILLARY ACTION

(75) Inventors: Jay Clark, Irvine, CA (US); Carl Churchill, Raleigh, NC (US)

(73) Assignee: Genomic Solutions Inc., Ann Arbor, MI (US)

( * ) Notice: Subject to any disclaimer, the term of this patent is extended or adjusted under 35 U.S.C. 154(b) by 0 days.

(21) Appl. No.: 10/889,538

(22) Filed: Jul. 12, 2004

(65) Prior Publication Data

US 2005/0112776 A1    May 26, 2005

Related U.S. Application Data

(60) Provisional application No. 60/486,479, filed on Jul. 11, 2003.

(51) Int. Cl.
*G01N 1/10* (2006.01)
(52) U.S. Cl. .................. 436/180; 422/99; 422/100; 422/101; 347/44; 347/74; 222/206; 222/210
(58) Field of Classification Search ......... 422/99–101; 436/180; 73/864.18; 222/206, 210; 347/44, 347/74
See application file for complete search history.

(56) References Cited

U.S. PATENT DOCUMENTS 5,460,782 A * 10/1995 Coleman et al. ............ 422/100
6,001,309 A * 12/1999 Gamble et al. ............. 422/100
6,309,891 B1 * 10/2001 Shalon et al. ............... 436/180
6,744,046 B2 * 6/2004 Valaskovic et al. .......... 250/288
2002/0190203 A1   12/2002 Valaskovic et al.
2003/0086828 A1 * 5/2003 Chiou et al. ................ 422/100

OTHER PUBLICATIONS

PCT International Search Report for International Application No. PCT/US04/22385, filed Jul. 12, 2004, 4 pages.

* cited by examiner

*Primary Examiner*—Jill Warden
*Assistant Examiner*—Jyoti Nagpaul
(74) *Attorney, Agent, or Firm*—Rader, Fishman & Grauer PLLC

(57) ABSTRACT

The present invention comprises a removable capillary tip insert which provides for replacement of an individual capillary in the dispensing head of an automated liquid handling apparatus. In some embodiments, the insert has been designed to accept variable capillary lengths while maintaining a constant length protruding from the insert. In a preferred embodiment, the removable capillary insert of the invention comprises a head adapted to accept an insertion tool and tapered to seat in the dispense head; a shaft with external threads which form a threaded collar that permits the insert to be screwed into the dispense head; a lumen running internally from the proximal to the distal ends of the head and shaft which forms a hollow interior in the insert in which a capillary resides; and a capillary tube of user-selected liquid capacity. One embodiment, without limitation, comprises a molded plastic part with an integral capillary tube. Other embodiments comprise dispensing heads with various configurations of capillary inserts and methods for automated liquid dispensing using the same.

1 Claim, 7 Drawing Sheets

FIGURE 3
A
B
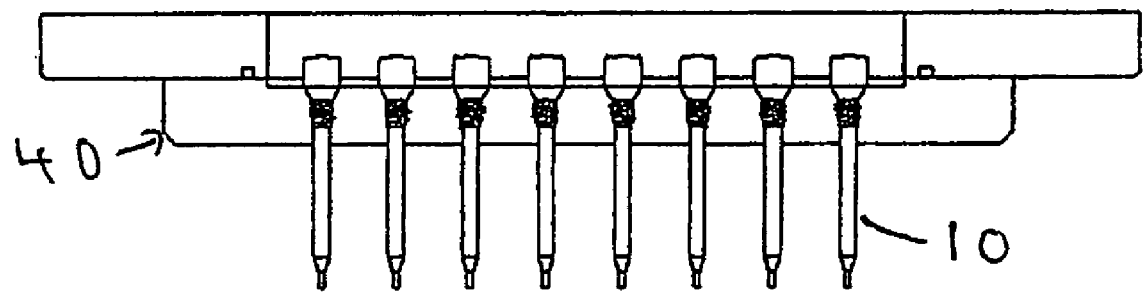
FIGURE 4

APPARATUS AND METHODS FOR LIQUID SAMPLE HANDLING BASED ON CAPILLARY ACTION

CROSS-REFERENCE TO RELATED APPLICATIONS

This application claims priority based on U.S. Provisional Patent Application No. 60/486,479, filed Jul. 11, 2003, which is hereby incorporated by reference in full.

FIELD OF THE INVENTION

The invention relates to the field of automated handling of liquid samples.

BACKGROUND

Advances in genomics, proteomics, combinatorial chemistry, and compound library management have each driven the need for increasingly fast, accurate methods of high throughput liquid sample handling. As information libraries broaden, so does the need to be able to conduct automated sample handling and screening in increasingly small volumes, including in nanoliter volumes. Researchers in biopharmaceutical and chemical companies, universities and other research institutions often seek automated research systems that significantly enhance productivity and improve other processes, such as drug discovery processes. Thus, cost-effective miniaturized screening essays, and related sample management, have assumed greater importance.

Several currently available technologies provide low-volume dispensing or delivery capability. Among others, these include "contact" and "noncontact" dispensing methodologies. Contact dispensing uses surface tension created by touching the dispensed droplet on the receiving substrate to remove the droplet from the dispensing apparatus.

Noncontact dispensing uses force or pressure, such as fluid or air pressure, to eject the droplet from the dispensing apparatus without contact first with the receiving substrate. Because dispensing can occur from the top of the well, plate processing times can be significantly faster when drops are dispensed serially "on-the-fly." Often these technologies are applied to liquid dispensing or handling applications involving standard 96-well, 384-well, 1536-well, and increasingly dense microtiter plates or other substrates.

The current trend in the high throughput screening ("HTS") market is to reduce the assay volume in order to reduce costs. This reduction is primarily accomplished with low volume, high-density microtiter plates such as 384-, 1536-, or 3456-well formats. As 1536-well and larger plates become more widely used for HTS applications, there is a need for practical, automated liquid handling solutions for both compound transfer and assay assembly.

As an example of one application, without limitation, compound libraries are being developed to store millions of potential drug compounds. Scientists must be able to not only store their compounds, but also to quickly retrieve and sample a single compound, thus demanding fast and accurate compound sampling.

Management of compound libraries often involves compound reformatting, whereby aliquots of samples in a liquid compound library are transferred from a "mother" plate onto another microtiter plate, the "daughter" plate, in which the user wishes to perform the test or assay. Because testing is increasingly performed on a smaller scale, there is a need to increase the density of sample plates. Thus, reformatting process may occur among "mother" and "daughter" plates of the same density, or among plates of different densities where samples from smaller-density plates are combined onto a larger density plates, as some examples, only, combining 96-well plates onto 384-well or 1536-well plates, and other permutations.

In addition, primary drug screening requires scientists to search through thousands of potential drug candidates to find out which ones show biological activity towards a target. The screening technology has progressed from a few 96-well plates and a few hundred interactions per year, to today's HTS. Techniques which enable researchers to perform complex, high volume experiments at a lower cost and in shorter time than traditional techniques facilitate faster and less expensive drug discovery.

In many cases, these processes are automated by combining incubators, centrifuges, plate readers, and aspirate and dispense robots together into a single platform, known as an integration robot. Each contributing component in the robot must operate efficiently, accurately, and with easy integration. Thus, an HTS robot can expect to present a 1536 well microtiter plate to the integration station, have all wells filled, and the plate removed in minutes, if not seconds.

Moreover, the sequencing of the human genome project has produced the fields of genomics and proteomics, which are global studies of an organism's gene and protein complements, respectively. A related field, structural genomics, has emerged which uses high throughput protein crystallography as its central platform to solve the structure for thousands of proteins.

In the past, protein crystallography has been a labor-intensive, low-throughput process. However, high-throughput protein crystallography involves using many automation concepts from HTS. The liquid handling requirements of protein crystallography are similar to those for HTS and include low sample volumes, high dispense speed (for example, to avoid evaporation of the mother liquor), and accurate dispense volumes.

Automated liquid handling apparatus perform a central role in such uses. By providing fast, accurate sample handling, such robots perform many types of laboratory functions, including as examples only, plate compressions or expansion from 96-, 384-, 1536- well or other microplates; plate replication and reformatting; reagent additions; and dilutions.

Technologies are currently available to perform automated liquid sample handling in light of the requirements for noncontact transfer of samples. Once such technology is the Hummingbird™ dispensing system (Cartesian Division of Genomic Solutions, Inc., Irvine, Calif.). The Hummingbird Technology is a robust, highly parallel solution for transferring compounds and creating assay plates for HTS, including the transfer of small volumes of liquids. This technology utilizes an array of capillaries to transfer very small nanoliter volumes of compounds, as desired.

The Hummingbird noncontact technology involves sipping or aspirating a sample from a source plate or other substrate using the capillary action of narrow-bore glass capillaries, followed by dispensing with a pulse of air. Sample transfer is accomplished by dipping an array of capillary tubes mounted in a mounting block into a source plate, filling the capillaries by capillary action, and dispensing into the destination plate or other substrate by applying pressure to the backside of the capillaries. The transfer volume is determined by the volume of the capillary tube.

The mounting block currently consists of an array of narrow-bore capillaries that are glued into a plastic plate. This allows for plate replication, plate duplication and plate reformatting, sample dilution and reagent addition. Hummingbirds can be operated in a standalone mode or via an ActiveX interface and configured with a robotic plate handler. in 96 or 384 well plates.

Such technologies allow for accurate, high-speed, non-contact, low volume aspirate and dispense systems, reagent addition and array printing, compound transfer, and assay assembly. However, the capillary tubes in the mounting blocks may become damaged or clogged, which can result in downtime. Moreover, because the capillary tubes are glued or molded fixedly in the mounting block, they are difficult to repair or replace. In addition, because the capillary tubes are fixed, it is challenging to adapt the current mounting block with glued or molded capillaries to applications where variability in sample size in a single microtiter plate may be desired.

Thus, there remains a need for improved apparatus and methods to overcome these drawbacks.

SUMMARY

The present invention was developed in light of these and other drawbacks. The present invention comprises a removable capillary tip insert which provides for replacement of an individual capillary in the dispense head of an automated liquid handling apparatus. In some embodiments, the insert has been designed to accept variable capillary lengths while maintaining a constant length protruding from the insert. In a preferred embodiment, the removable capillary insert of the invention comprises a head adapted to accept an insertion tool and tapered to seat in the mounting block of the dispense head; a shaft with external threads that form a threaded collar that permits the insert to be screwed into the mounting block; a lumen running internally from the proximal to the distal ends of the head and shaft which forms a hollow interior in the insert in which a capillary resides, and a capillary tube of user-selected liquid capacity. One embodiment, without limitation, comprises a molded plastic part with an integral capillary. Other embodiments comprise mounting blocks with various configurations of the capillary insert and methods for automated liquid dispensing using the same.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which:

FIGS. 3(A)-(B) are ghost perspectives of capillary inserts of different capillary capacities which have a uniform length by which the capillary tube protrudes from the distal end of the insert's shaft.

FIG. 4 is a side ghost perspective of a mounting block with a plurality of inserts.

DETAILED DESCRIPTION

Figure 1:
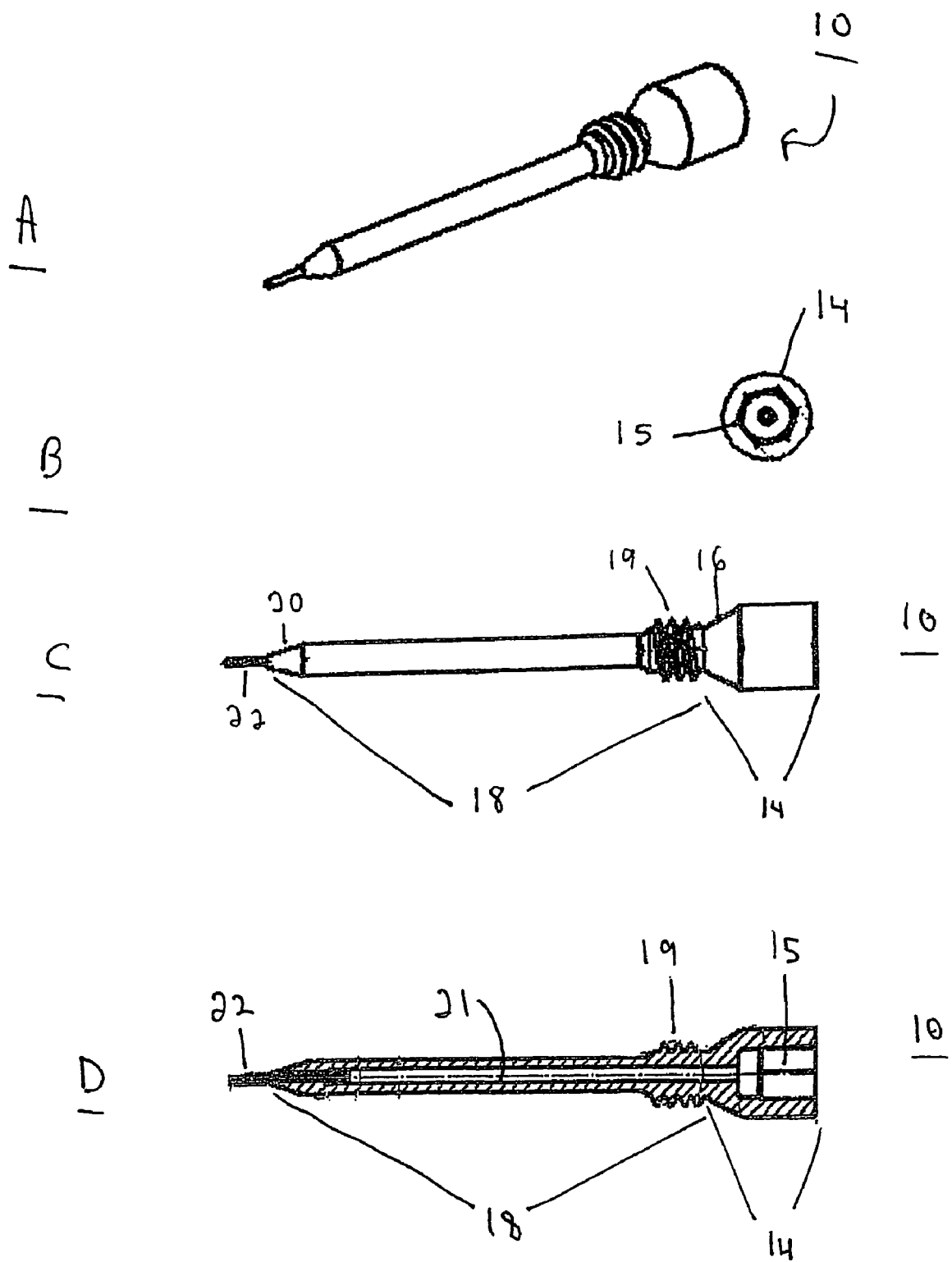
FIGS. 1(A)-(D) are side, top, side and ghost perspectives, respectively, of a capillary tip insert comprising the invention.

The invention comprises a capillary tip insert 10 for an automated liquid dispensing apparatus for small liquid volumes and methods for using same. The insert 10 is comprised of a head 14 and a shaft 18, into which a capillary tube 22 of desired liquid capacity is fastened. In use, the capillary tube 22 of the insert 10 fills with sample aliquots by capillary action, and the aliquot is later dispensed by air pressure. The invention also comprises an improved mounting block 40 for better manufacturing and maintenance.

To provide the replacement of an individual capillary in a dispensing head, a removable insert 10 has been designed which fits into a mounting block 40. The insert 10 has a hollow interior in which at least a portion of the capillary tube 22 resides. In some embodiments of the invention, without limitation, the insert 10 has been designed to accept variable capillary tube 22 lengths while maintaining a constant length protruding from distal end of the insert's shaft 18. A threaded collar 19 permits the insert 10 to be screwed securely into the mounting block 40.

Turning to FIGS. 1(A)-(B), in a preferred embodiment, without limitation, the invention is comprised of a capillary tip insert 10 with various regions, including a head 14, shaft 18, and a capillary tube 22 which is inserted and fastened into the distal end of the shaft 18. In general, the insert 10 is cylindrical along its longitudinal axis. Running from the proximal end of the insert 10 to its distal end is an internal lumen 21. The lumen 21 may be of one diameter or of varying diameter along the axis through the insert 10, depending on the desired configuration of the tip. At the proximal end of the insert 10, the head 14 is generally cylindrical with a diameter between 1 and 4 mm, preferably 2.5 mm. The internal region of the head 14 is formed in a shape, such as a hexagonal shape 15, to act as a receptacle for a tool, such as an Allen wrench (e.g., FIG. 1(B)), in order to turn the insert 10 and fasten it into place in the mounting plate 40.

Distally from its top, the head 14 tapers until it reaches the diameter of the shaft 18, thus forming a cone 16. The cone 16 acts as a seal in the mounting plate 40 when the insert 10 is put in place and fastened with a tool. The degree of the cone's taper may be selected by the user, although an angle of about 60° is preferred.

The shaft 18 of the insert 10 is cylindrical and also comprises external spiral threads 19 at its proximal end, as well as a taper 20 at its distal end. The taper 20 may be selected by the user, although a taper of approximately 33° is preferred. Upon insertion into the mounting plate 40, the external spiral threads 19 at the proximal end of the shaft 18 contact the mounting plate, and when turned in the appropriate direction, fasten and seal the insert 10 in the mounting plate 40.

A capillary tube 22 of user-selected liquid capacity is joined to the distal end of the shaft 18. In a preferred embodiment, the capillary tube 22 is joined to the shaft 18 by molding the distal end of the shaft 18 around at least a portion of the capillary tube 22. In some other embodiments, without limitation, the capillary tube 22 is inserted and glued in place into the distal end of the shaft 18, using adhesives known in the art, as one example only and without limitation, dimethyl sulfide-compatible adhesives. In preferred embodiments, without limitation, the liquid capacity of the capillary tubes may be selected from a range of between 1 and 10,000 nanoliters, inclusive. The liquid capacity volumes of capillary tubes 22 may be selected by the user as desired for a particular application. In some embodiments, the liquid capacity of the capillary tube 22 may be varied by adjusting the inner diameter and/or length of the capillary tube. The capillary tubes 22 are manufactured according to methods known to those of ordinary skill in the art such that the liquid volume capacity taken up by the capillary tube 22 is predictable within acceptable standards in the industry.

In a preferred embodiment, without limitation, the head 14 and shaft 18 of the insert 10 may be made of polypropylene, polystyrene, or other suitable materials known to those of ordinary skill in the art. In similar fashion, the capillary tube 22 of the invention may be comprised of glass, polyethylethylketone (PEEK), or other suitable materials known to those of ordinary skill in the art.

Figure 2:
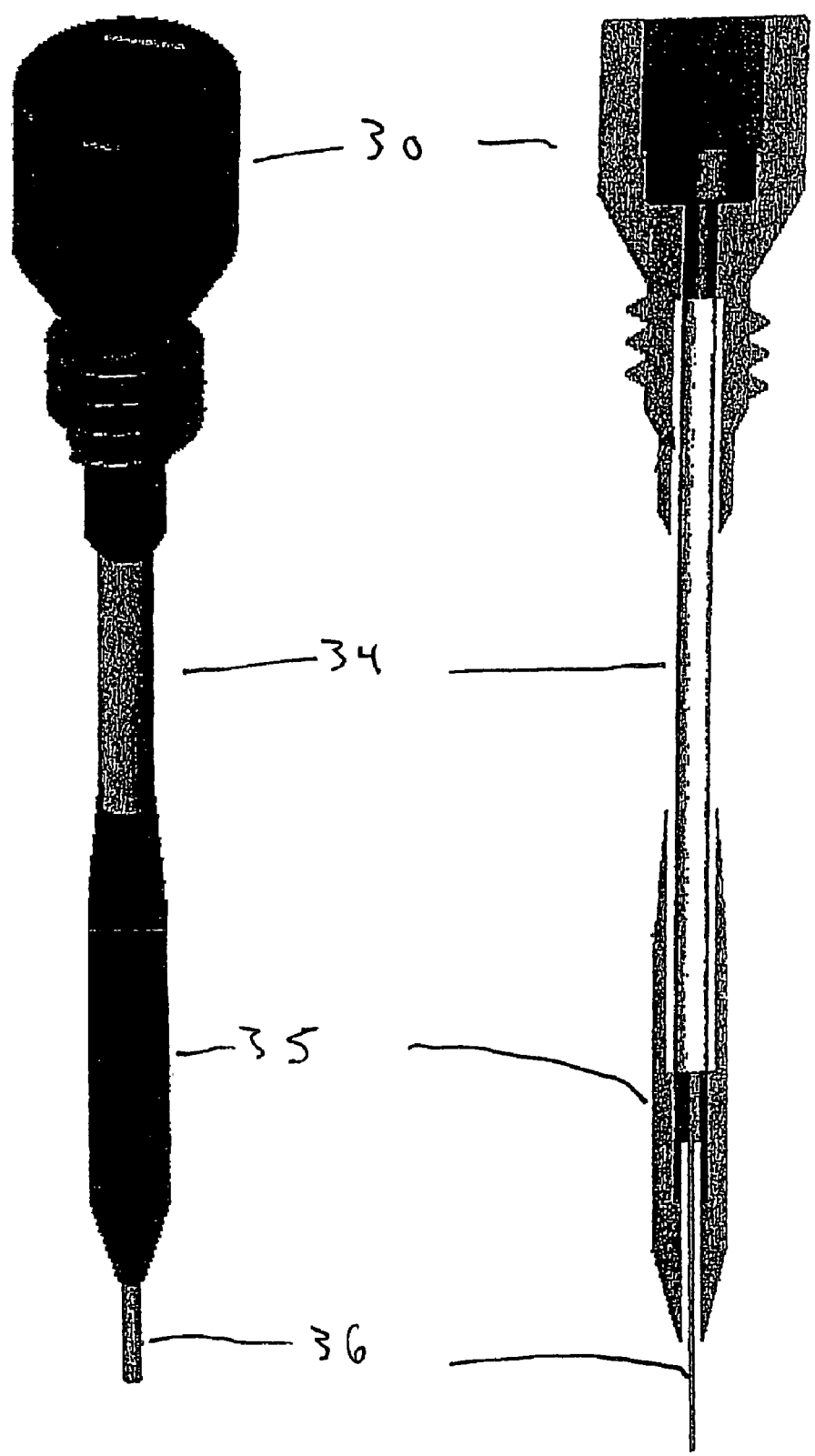
FIG. 2 is side perspectives of one embodiment of the capillary tip insert, without limitation.

Embodiments of the invention may include, without limitation, an array of inserts made by molding, assembly, straight molding, or combinations thereof. Inserts, whether individual or molded, could also comprise capillary tubes within the inserts. In some preferred embodiments, without limitation, the head 14 and shaft 18 of the insert 10 may be blow-molded as single piece in which the capillary tube 22 is fastened, or the insert may be comprised of separate head, shaft, and capillary tube components which are assembled. For example in the latter embodiment (see FIG. 2), the head 30 may be molded plastic, the shaft 34 may be of stainless steel, with a molded plastic connector 35 forming a connector and seat between the capillary tube 36 and the shaft 34 at the distal end of the shaft.

The overall length of capillary inserts 10 comprising the invention may be selected and varied by the user depending on factors such as the desired density of the sample plates and depth of sample sources, as examples only, wells or other receptacles. In preferred embodiments, the total length of the capillary insert 10 is between 22 and 32 mm, with the most preferred embodiment comprising a length of about 27 mm. The relative lengths of the head 14 and shaft 18 may also be selected and varied by the user, although in preferred embodiments, the head 14 will be between 3-7 mm in length, and the shaft 18 will be from 17 to 25 mm in length. The capillary tube protrudes from the distal end of the shaft region by approximately 1 to 3 mm, with a distance of about 2 mm most preferred.

The maximum diameter of capillary inserts 10 comprising the invention may also be selected or varied by the user according to criteria such as the density of sample sources, by way of examples only, microtiter plate wells or other receptacles and space available on the mounting plate 40. In preferred embodiments, the maximum diameter of the head 14 is between 1.5 to 5 mm, with about 4 mm most preferred. In preferred embodiments, the maximum diameter of the shaft 18, not including the diameter of the external threads, is between 0.5 and 2.0 mm, with about 1.5 mm most preferred.

In accordance with the invention, in some embodiments, capillary tubes 22 of variable length and capacity can be selected for use in different inserts 10, while maintaining the distance by which the distal end of the capillary tube 22 protrudes from the distal end of the shaft 18(see FIGS. 3(a) and 3(b)). Thus, in some embodiments, the mounting plate of the invention may contain capillary inserts of different liquid capacity while maintaining a uniform distance between the bottom of the mounting plate and the distal end of the inserts 10.

Figure 5:
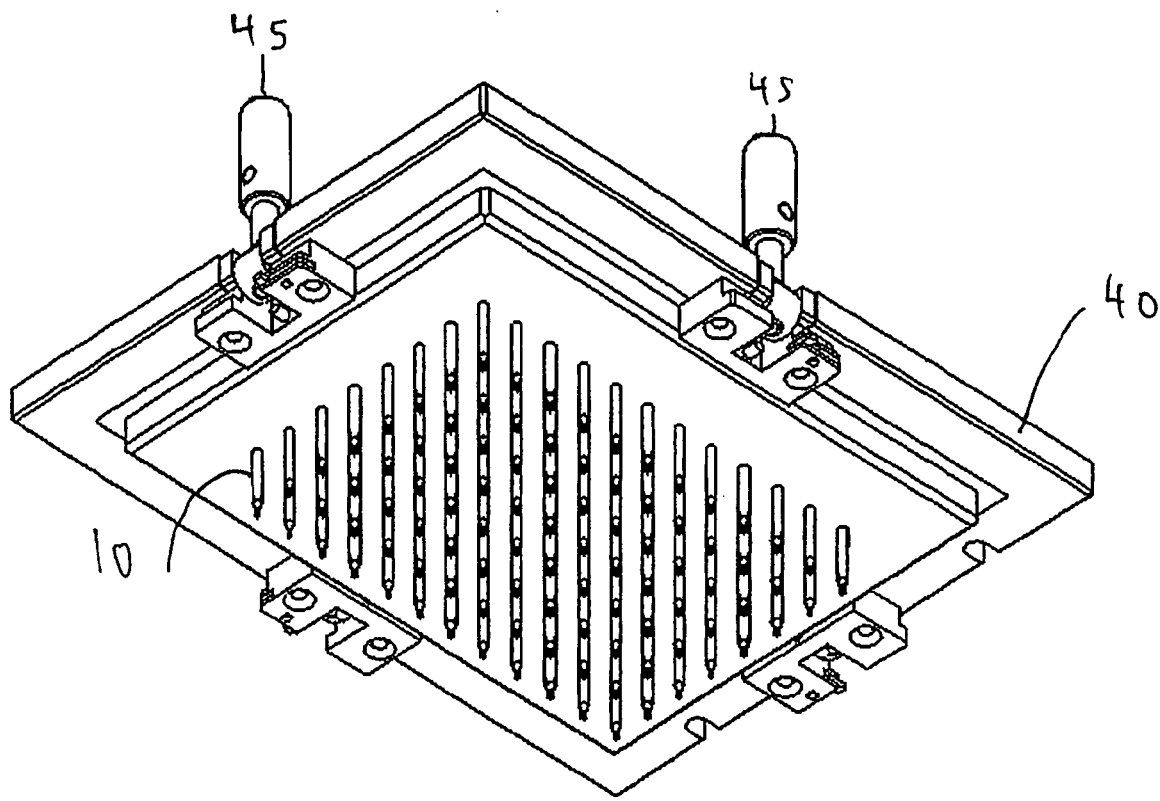
FIG. 5 is a bottom perspective of a mounting block of the invention.
Figure 6:
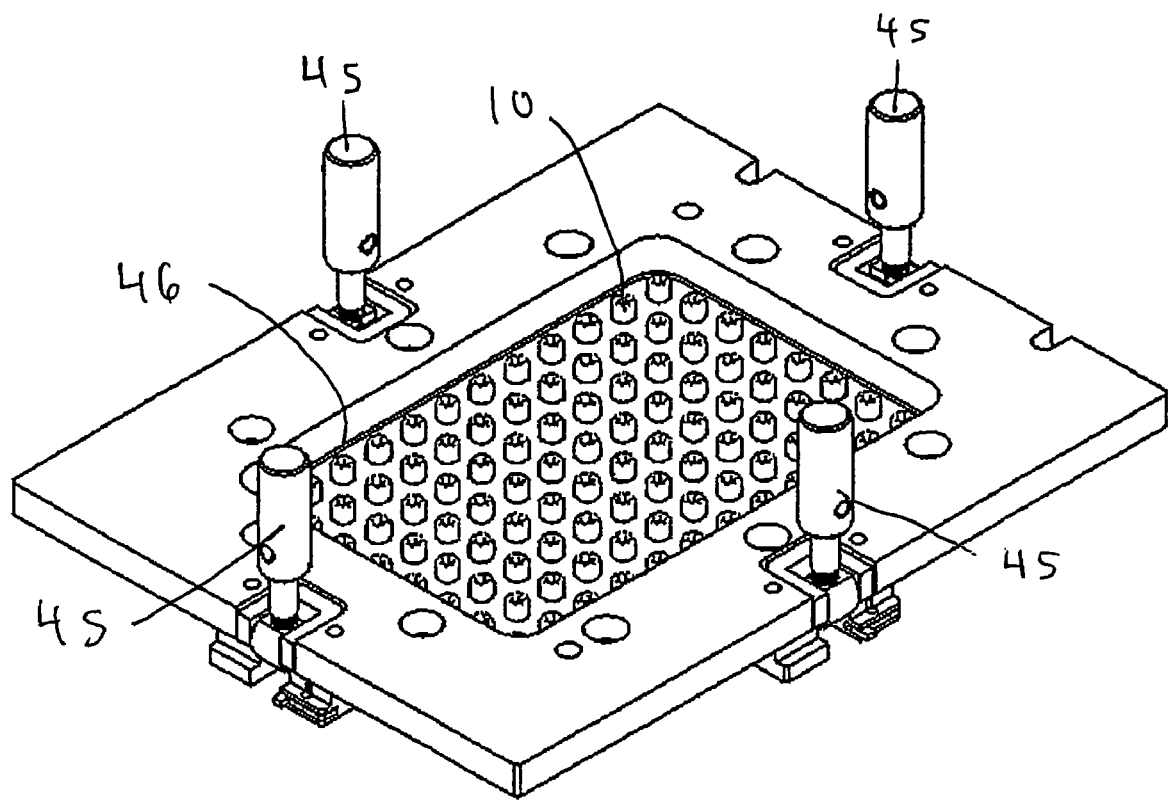
FIG. 6 is a top perspective of a mounting block of the invention.

In some embodiments, the invention comprises a mounting block 40 into which a plurality of inserts 10 is attached and seated. (FIGS. 5 and 6). The mounting block may be made from metal, plastic or other suitable material known to those of ordinary skill in the art. The mounting block may be comprised of a plurality of machined openings (not shown in detail) designed to accept the capillary inserts 10. The openings in the mounting block are machined in a manner that corresponds with the threads and conical sides of the head of the insert 10 so that when the insert is inserted and fastened by torquing with an insertion tool, a seal is created and the insert 10 is firmly fastened in place. Thus, in some embodiments, the seats for the inserts 10 in the mounting block 40 comprise threaded holes formed to nest tightly with the cone shape of the head 14 once the insert 10 is screwed into the hole in the block 40.

The mounting block 40 may contain a plurality of inserts 10, as desired by the user. Solid threaded caps (not shown) may be inserted into the holes in the mounting block 40 where the user does not wish to place a capillary insert. Mounting blocks 40 may include a plurality of tips, by way of examples only, in 96-, 384-or 1536-well formats.

In some embodiments, the mounting block 40 is further comprised of one or more clamps 45 which facilitate the attachment of the mounting block 40 to an automated liquid dispensing apparatus. In one embodiment, without limitation, the clamp is comprised of a capped bolt mounted on a rotating member and attached to the mounting plate 40 such that the capped bolt may be moved from vertical to at least horizontal position in relation to the top face of the mounting block 40. (See FIG. 5). When the mounting block 40 is to be fastened to the dispensing machine, the clamp 45 is moved to a vertical position and latched over a catch in the dispensing apparatus (not shown) in a manner that produces a tight seal between the mounting block 40 and the dispensing apparatus. One of ordinary skill will also recognize that there are also other clamping means to accomplish the same goal.

In some embodiments, the top surface of the mounting block 40 is comprised of one or more orifices 46 for application of the air pressure in order to take up or dispensing liquid samples from the inserts 10. (See FIG. 6). In some preferred embodiments, without limitation, the orifices 46 may be such that air pressure may be applied collectively to a plurality of inserts 10 for discharge of liquid samples from the capillary tubes 22. In other embodiments, orifices may be configured to route air pressure to one or more selected capillary inserts 10 for dispersal of samples into particular sample receptacles or wells via individual tips.

In some embodiments, the capillary inserts 10 may be color-coded with different colors so that the user may select or monitor the dispersal of samples from different regions of the mounting block 40. Moreover, in some embodiments, without limitation, the mounting block 40 may be comprised of capillary inserts 10 of different liquid capacities so that such that different liquid volumes may be disbursed into the sample receptacles, as one example only, microtiter plates, according to user-selected criteria. Thus, embodiments of the invention may comprise, without limitation, replaceable capillaries of varying length, with or without color coding, and inserts and/or capillary tubes with a plurality of dispense volumes.

Figure 7:
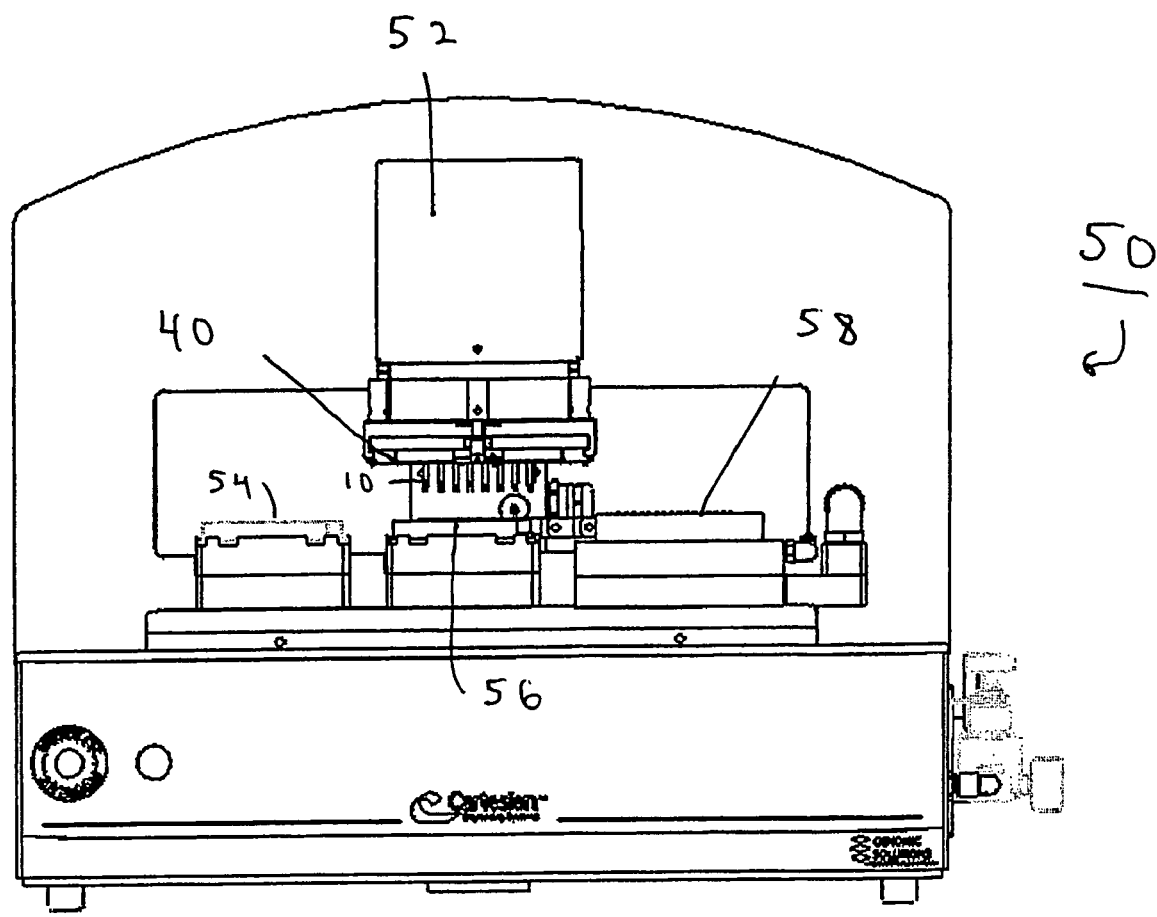
FIG. 7 is a front perspective of an automated liquid sample handling apparatus containing the invention.
Figure 8:
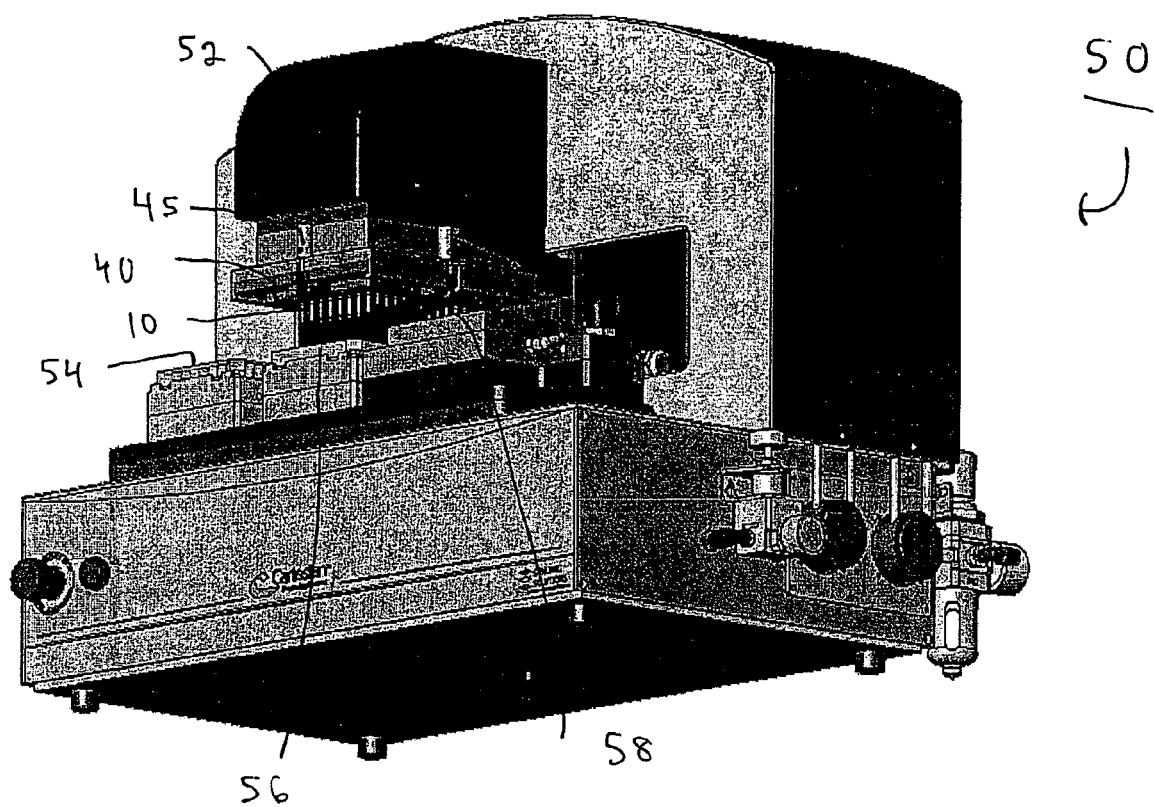
FIG. 8 is another perspective of an automated liquid sample handling apparatus containing the invention.

In use, the mounting block 40 is mounted and clamped to a dispensing head 52 of an automated liquid dispensing apparatus 50, as one example only, the Hummingbird dispensing machine (Genomic Solutions, Inc., Irvine, Calif.). (See FIGS. 7 and 8). The Hummingbird technology involves sipping of sample from a sample source plate 54 using narrow-bore glass capillaries 22, followed by dispensing with a pulse of air. Transfer occurs by aspirating samples using capillary action, followed by dispensing with a pulse of air. This allows for plate replication, plate duplication, plate reformatting, and other dispensing tasks that may be of interest to the user.

The dispensing head 52 is cycled between sample trays in order to take up and aspirate samples as the user desires. As only one example of a use, without limitation, the dispense head 52 may cycled to a sample source plate 54, withdraw sample aliquots by capillary action of the inserts 10, and cycle to a sample destination plate 56, where the aliquots are dispersed by air pressure. Intermittently the dispensing head 52 may be cycled to a wash station 58 where the inserts 10 may be rinsed as desired.

The insert 10 of the invention provides several advantages over the prior art. The insert 10 may allow the capillary tube 22 to reach the bottom of deep well plates while still using an acceptable capillary length and inner diameter (i.e., if only a capillary was used to reach into deep well plates, the inner diameter would be prohibitively small). The mounting block 40 can be manufactured with discrete inserts 10, tested, and the failed inserts can be easily replaced. Likewise, the user can replace the insert 10 if the capillary tube 22 clogs or breaks. The length of the insert 10 permits a wide range of capillary tubes 22 to be used which results in a wide range of transfer volumes. Current mounting heads must have capillary lengths long enough to dip into sample solutions. By using a very short capillary tube 22 with the insert 10, transfer volumes can be achieved.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

The invention claimed is:

1. A method for automated dispensing of liquid samples, comprising the steps of:
   providing a mounting block for an automated liquid dispensing apparatus comprising:
      one or more removable capillary tip inserts comprising a head, a shaft with external threads, an internal lumen extending the lengths of the head and the shaft, and a capillary tube having a distal end, the capillary tube joined to a distal end of the shaft opposite said head, the distal end of the capillary protruding from the distal end of the shaft, the capillary tube being configured to draw a liquid therein through its distal end by capillary action;
      a surface comprising a plurality of holes configured to accept the external threads and shapes of the inserts; and
      one or more orifices for the application of air pressure to one or more of the inserts;
   providing a source substrate containing one or more liquid samples;
   providing a destination substrate for one or more liquid samples;
   providing an automated liquid dispensing apparatus comprising:
      a dispensing head;
      means to cycle the dispensing head between source and destination substrates; and
      means to selectively apply air pressure to one or more of the removable capillary tip inserts;
   configuring the mounting block to fasten to the dispensing head; and
   cycling the mounting block between the source substrate and the destination substrate, such that a portion of one or more samples from the source substrate is taken up by one or more inserts on the mounting plate by capillary action and dispensed onto the destination substrate by selective application of air pressure to the insert.

* * * * *